United States Patent [19]

Wirth

[11] Patent Number: 5,196,585
[45] Date of Patent: Mar. 23, 1993

[54] PROCESS FOR TREATING DINITROANILINES WITH SULFITE TO REDUCE IMPURITIES AND TO REDUCE THE ABILITY TO PRODUCE NITROSAMINES

[75] Inventor: David D. Wirth, Lafayette, Ind.
[73] Assignee: DowElanco, Indianapolis, Ind.
[21] Appl. No.: 591,590
[22] Filed: Oct. 2, 1990
[51] Int. Cl.$^5$ .................................... C07C 209/84
[52] U.S. Cl. .................................... 564/437
[58] Field of Search .................................... 564/437
[56] References Cited

U.S. PATENT DOCUMENTS

| | | | |
|---|---|---|---|
| 4,139,562 | 2/1979 | Yamamoto | 564/439 |
| 4,440,962 | 4/1984 | Pallucca | 568/933 |
| 4,501,608 | 2/1985 | Cannon | 71/DIG. 1 |
| 4,874,895 | 10/1989 | Graziello | 564/437 |

FOREIGN PATENT DOCUMENTS 0697087  11/1964  Canada .................................... 564/437

*Primary Examiner*—Marianne M. Cintins
*Assistant Examiner*—Michael B. Hydorn
*Attorney, Agent, or Firm*—Alice A. Brewer; Donald R. Stuart

[57] ABSTRACT

The present invention is directed toward a process of treating crude dinitroaniline with an aqueous sulfite solution as a method of stabilizing the herbicide against formation of nitrosamines and of reducing impurities therein.

5 Claims, No Drawings

PROCESS FOR TREATING DINITROANILINES WITH SULFITE TO REDUCE IMPURITIES AND TO REDUCE THE ABILITY TO PRODUCE NITROSAMINES

BACKGROUND OF THE INVENTION

The danger of nitrosamines is well known. Nitrosamines exercise an acute hepatotoxic action, and are carcinogenic, mutagenic and teratogenic. The presence of nitrosamines in dinitroanilines, even in quantities of a few ppm, is considered undesirable. Much effort has been directed to the removal of nitrosamines in dinitroanilines. See, e.g., U.S. Pat. Nos. 4,127,610; 4,185,035; and 4,226,789.

The removal of nitrosamines from dinitroanilines does not necessarily eradicate all residual nitrosating species. A dinitroaniline which shows only a negligible nitrosamine content may subsequently develop a higher nitrosamine level. This occurs if the dinitroaniline herbicide containing residual nitrosating agent is formulated with or exposed to secondary amines which may be, for example, either an impurity in the formulation or a naturally occurring amine.

Circumstances which favor nitrosamine formation present a problem. Processes to stabilize dinitroanilines against subsequent nitrosamine formation have been disclosed in U.S. Pat. No. 4,501,608 where a method of stabilizing dinitroanilines against the formation of nitrosamines by the incorporation of an addition compound comprising a bisulfite in conjunction with an aldehyde or ketone is disclosed. U.S. Pat. No. 4,440,962 discloses a process for obtaining dinitroanilines free from nitrosating agents by treatment of a dinitrochloro precursor to the dinitroaniline with an 1% to 5% aqueous bisulfite solution at a temperature of 50° C. to 100° C. and at a pH of from 1 to 3 for 1 to 3 hours.

Additionally, the presence of chloroaromatic impurities in dinitroaniline herbicides is problematic in that these impurities have been implicated as being responsible for a drop in pH upon formulation with other herbicides and bases such as ammonia.

It would be desirable to have a single process which would both reduce chloroaromatic impurities as well as stabilize dinitroanilines against subsequent nitrosamine formation.

DESCRIPTION OF THE INVENTION

The present invention is a process of treating crude dinitroanilines with an effective amount of sulfite in order to reduce chloroaromatic and other impurities in the dinitroaniline and in order to stabilize the compound against the formation of nitrosamines.

Sulfites suitable for the purpose of this invention are inorganic and water soluble sulfites, and include such sulfites as sodium sulfite, potassium sulfite, ammonium sulfite, lithium sulfite, zinc sulfite, barium sulfite, magnesium sulfite, and ferrous sulfite. These sulfites are well known and each sulfite is readily available. The compounds preferred for use in this invention are sodium sulfite, potassium sulfite and ammonium sulfite. The most preferred sulfite for the purpose of this invention is sodium sulfite.

The present invention requires the use of an effective amount of sulfite to be operable. An effective amount of sulfite for the purposes of this invention is that amount which causes a reduction in the ability of the dinitroaniline treated to form nitrosamines and which reduces the level of chloroaromatic and other impurities therein. The amount of sulfite employed in accordance with the present invention is not critical and will vary with such factors as the identity of the dinitroaniline treated, the amount, if any, of residual nitrosating species, the severity of intended subsequent conditions, and the like. In general, the sulfites utilized in this invention typically are effective when present in a concentration of from about 0.25 to about 3 percent of the dinitroaniline by weight. A preferred concentration is from about 1 percent to about 2 percent.

The sulfite used according to this invention is utilized in aqueous solution. The ratio of the aqueous sulfite solution to the dinitroaniline to be treated is not particularly critical, and is typically between about 0.1 and about 0.3 liters of aqueous sulfite solution per kilogram of dinitroaniline. Greater volumes of solution show no improvement in the results while they increase the cost of treatment, and an excessively low value of said ratio makes contact between the two liquid phases less efficient during the treatment. The preferred ratios of sulfite solution to dinitroaniline are from about 0.15 to about 0.25 liters/kilogram.

The process of treating dinitroanilines with sulfite solution is carried out at a temperature above the melting point of the dinitroaniline and below the boiling point of water. Typically, this temperature will range from about 60° C. to about 90° C., preferably between from about 70° C. to about 80° C. The reaction time for each treatment is not critical and ranges from about 20 minutes to about 2 hours, a time of about 45 minutes to about 75 minutes being preferred depending on such factors as the concentration and ratio of sulfite solution utilized, the temperature, the degree of purity desired, and the like. The pressure under which the treatment is undertaken is not critical, and the treatment could be run under pressure, if desired. However, typically, for convenience, the treatment is carried out at atmospheric pressure.

The pH during the process of treating dinitroanilines with sulfite is kept at from about 9 to about 10.5 and should not fall below about 8 or exceed about 11 for the process to be effective. Preferably, the pH is kept at from about 9.5 to about 10.5.

This invention can be practiced at one or more of several stages in any standard dinitroaniline purification processes that is compatible with the above conditions. Known and standard processes for purification of dinitroanilines consist of, for example, washing the crude dinitroaniline first with an acid wash, then with water, and finally with sodium carbonate prior to isolation and drying of the purified product. The present invention may be introduced into such a standard process in any of several places such as prior to the acid wash, prior to or in place of the sodium carbonate wash, or prior to or in place of the sodium carbonate wash with subsequent acid and water washes. It is preferred to replace the sodium carbonate wash with the sodium sulfite wash or washes for simplicity. It has been found that sequential treatments of the dinitroaniline with aqueous sulfite solution is beneficial. This is accomplished by contacting the dinitroaniline with aqueous sulfite, separating off the aqueous layer, and repeating the sequence with fresh solution.

Generally, whenever the sulfite solution is introduced, it is mixed with the crude dinitroaniline under strong agitation to assure uniform contact between the sulfite solution and the dinitroaniline. The sulfite may be contacted with the dinitroaniline while the dinitroaniline is in a molten state or while it is in solution. Additionally, this invention may be practiced in dinitroaniline production where the product is produced by the batch or continuously, and this invention may be practiced either as a single treatment of the dinitroaniline, or as more than one treatment of the dinitroaniline.

Subsequent to the completion of standard purification procedures and the sulfite treatment, the purified product is isolated using standard and well known procedures to yield an improved dinitroaniline product. This process is useful for the removal of impurities such as 1-chloro-2,6-dinitro-4-(trifluoromethyl)benzene and 1-chloro-2,4-dinitro-6-(trifluoromethyl)benzene, which are responsible for a detrimental drop in the pH of formulated dinitroanilines. This invention also removes other minor impurities which have been identified by gas chromatography and mass spectrometry as isomers of chlorodinitrotrifluoromethylbenzene and dichloronitrobenzotrifluoride. Products of the reaction of these impurities and sulfite all remain in the aqueous layer. No new impurities are detected in the dinitroaniline. Additionally, this process is useful for the reduction of the ability of the treated dinitroaniline to form nitrosamines when formulated with materials which contain secondary amines.

Stabilization and purification of a dinitroaniline in accordance with the present invention can be practiced where the active ingredient of a formulated product is a dinitroaniline alone or is a combination of a dinitroaniline and another herbicide. Such formulations may contain solvents, buffers and emulsification agents according to procedures and formulations well known in the art. Combining treated dinitroanilines with other herbicides which contain secondary amines as contaminants is particularly beneficial.

Dinitroanilines are a well-known class of compounds. Dinitroanilines with which the present invention can be practiced (and their generic names) are:

4-trifluoromethyl-2,6-dinitro-N,N-di-n-propylaniline (trifluralin);
4-trifluoromethyl-2,6-dinitro-N-n-butyl-N-ethylaniline (benefin);
4-trifluoromethyl-2,6-dinitro-N-ethyl-N-methallylaniline (ethalfuralin);
4-isopropyl-2,6-dinitro-N,N-di-n-propylaniline (isopropalin);
4-tert-butyl-2,6-dinitro-N-sec-butylaniline (butralin);
3,4-dimethyl-2,6-dinito-N-(1-ethylpropyl)aniline (pendimethalin);
4-trifluoromethyl-2,6-dinitro-N-propyl-N-(2-chloroethyl)aniline (fluchloralin);
4-trifluoromethyl-2,6-dinitro-N-propyl-N-(cyclopropylmethyl)aniline (profluralin);
4-trifluoromethyl-2,6-dinitro-3-amino-N,N-diethylaniline (dinitramine);
4-methyl-2,6-dinitro-N,N-bis(1-chloroethyl)aniline (chlornidine);
4-sulfamoyl-2,6-dinitro-N,N-di-n-propylaniline (oryzalin);
4-(methylsulfonyl)-2,6-dinitro-N,N-di-n-propylaniline (nitralin);
N-((4-dipropylamino)-3,5-dinitrophenyl)sulfonyl-S,S-dimethylsulfilimine (prosulfalin);
4-(trifluoromethyl)3-amino-2,6-dinitro-N,N-di-n-propylaniline (prodiamine).

Preferred dinitroanilines with which the present invention is carried out are trifluralin, benefin and ethalfuralin.

The following specific examples are presented to illustrate the process which is this invention, but they should not be construed as limiting the scope of this invention in any way.

EXAMPLE 1

TREATMENT OF TRIFLURALIN—(4-Trifluoromethyl-2,6-dinitro-N,N-di-n-propylaniline)

Molten crude trifluralin (800 g) was placed in a 1000 mL round bottomed flask fitted with a mechanical agitator The crude material was washed for one hour at 70° C. with 16.8 mL concentrated hydrochloric acid. Vigorous agitation was used during the washing operations for all procedures described. The phases were separated and the trifluralin was washed with 260 mL water at 70° C. for one hour. The phases were separated again and 200 g portions of the trifluralin were removed for further treatment as follows:

A. Control. A 200 g portion of trifluralin was washed at 70° C. for 30 minutes with a solution of 1.6 g sodium carbonate dissolved in 42 mL water. The phases were separated and the product dried for 30 minutes by vigorous agitation at 70°–80° C. under a vacuum of about 50 mm Hg.

B. One Sulfite Treatment. A second 200 g portion was washed with a solution of 2.5 g sodium sulfite in 50 mL water at 70° C. for two hours. The phases were separated and the product dried as in A.

C. Two Sulfite Treatments. A third 200 g portion of trifluralin was washed with a solution of 2.5 g sodium sulfite in 50 mL water at 70° C. for two hours. The phases were separated and the material was washed again with a fresh solution of 2.5 g sodium sulfite in 50 mL water at 70° C. for two hours. The phases were separated and the product was dried as described in A above.

The products from these three procedures were assayed for di-n-propylnitrosamine, total nitrosatable amines (the amount of di-n-propylnitrosamine produced from treatment of the sample with excess sodium nitrite solution), and nitrosating capacity. The first two of these assays were performed by gas chromatography/thermal energy analyzer as described in the literature. The latter assay was performed by addition of two or three drops of diisopropylamine to 3.00 g molten dinitroaniline in a vial. The contents were mixed and heated at 70° C. for one hour. The sample was then diluted with butyl chloride, chromatographed on alumina, concentrated in-vacuo, and analyzed on the standard gc/tea instrument. Results are reported below as ppm, the first two using di-n-propylnitrosamine as a standard and the latter using diisopropylnitrosamine as a standard.

TABLE I

| Treatment | Dipropylnitrosamine (ppm) | Total Nitrosatable Amines (ppm) | Nitrosating Capacity (ppm) |
|---|---|---|---|
| A | 0.05 | 0.33 | 3.61 |
| B | 0.08 | 0.57 | 1.58 |
| C | less than 0.03 | 0.11 | less than 0.03 |

EXAMPLE 2

Molten crude trifluralin (800 g) was placed in a 1000 mL round bottomed flask fitted with a mechanical agitator. The crude material was washed for one hour at 70° C. with 16.8 mL concentrated hydrochloric acid. Vigorous agitation was used during the washing operations for all procedures described. The phases were separated and the trifluralin was washed with 260 mL water at 70° C. for one hour. The phases were separated again and the material was treated with a solution of 10 g sodium sulfite dissolved in 160 mL water at 85° C. for two hours. The phases were separated and the wash was repeated for two hours with a fresh solution of 10 g sodium sulfite in 160 mL water at 85° C. The phases were separated and a portion of the product was dried in-vacuo at 60°-70° C. for about one hour. Analytical characterization was performed on this sample and compared to the material before the sulfite treatment.

TABLE II

| Assay | Before Sulfite | After Sulfite |
| --- | --- | --- |
| 1-chloro-2,6-dinitro-4-(trifluoromethyl)benzene | 0.09% | <0.02% |
| 1-chloro-2,4-dinitro-6-(trifluoromethyl)benzene | 0.47% | <0.02% |
| Di-n-propylnitrosamine | 0.02 ppm | <0.02 ppm |
| Total Nitrosatable Amines | 0.07 ppm | 0.06 ppm |
| Nitrosating Capacity | 3.1 ppm | <0.02 ppm |
| 3,4-dichloro-5-nitrobenzotrifluoride | 1.5% | 1.03% |

These results demonstrate that the level of chloroaromatic impurities is reduced by treatment with sulfite.

EXAMPLE 3

TREATMENT OF ETHALFLURALIN—4-Trifluoromethyl-2,6-Dinitro-N-methyallylaniline Technical grade molten Ethalfluralin (500 g) which had been subjected to the standard purification washes with hydrochloric acid, water, and sodium carbonate was placed in a 1 L flask which had been fitted with a mechanical agitator. The dinitroaniline was washed with 100 mL of a solution which was prepared by dissolving 31.26 g sodium sulfite in 200 mL water. The washing was performed at 70° C. for one hour. The phases were separated and the washing repeated under the same conditions with fresh sulfite solution. A portion of the purified ethalfluralin was dried in-vacuo at 60° C. overnight and subjected to the same assays as reported in Examples 1 and 2.

TABLE III

| Assay | Before Sulfite | After Sulfite |
| --- | --- | --- |
| 1-chloro-2,6-dinitro-4-(trifluoromethyl)benzene | 0.09% | 0.09% |
| 1-chloro-2,4-dinitro-6-(trifluoromethyl)benzene | 0.38% | <0.01% |
| N-ethyl-N-methallylnitrosamine | 0.01 ppm | 0.03 ppm |
| Total Nitrosatable Amines | 0.14 ppm | 0.06 ppm |
| Nitrosating Capacity | 4.03 ppm | 0.44 ppm |

EXAMPLE 4

TREATMENT OF BENEFIN—4-trifluoromethyl-2,6-dinitro-N-n-butyl-N-ethylaniline

Technical grade molten Benefin (500 g) which had been subjected to the standard purification washes with hydrochloric acid, water, and sodium carbonate was placed in a 1 L flask which had been fitted with a mechanical agitator. The dinitroaniline was washed with 100 mL of a solution which was prepared by dissolving 31.26 g sodium sulfite in 200 mL water. The washing was performed at 80° C. for one hour. The phases were separated and the washing repeated under the same conditions with fresh sulfite solution. A portion of the purified ethalfluralin was dried in-vacuo at 60° C. overnight and subjected to the same assays as reported in Examples 1 and 2.

The data described in Examples 3 and 4 demonstrate that the nitrosating capacity of dinitroanilines is reduced by sulfite treatment.

TABLE IV

| Assay | Before Sulfite | After Sulfite |
| --- | --- | --- |
| 1-chloro-2,6-dinitro-4-(trifluoromethyl)benzene | 0.17% | 0.004% |
| 1-chloro-2,4-dinitro-6-(trifluoromethyl)benzene | 0.49% | <0.005% |
| N-butyl-N-ethylnitrosamine | 0.02 ppm | <0.01 ppm |
| Total Nitrosatable Amines | 0.19 ppm | 0.05 ppm |
| Nitrosating Capacity | 2.82 ppm | 0.15 ppm |

It should be apparent to one of ordinary skill in the art that changes and modifications can be made to this invention without departing from the spirit or scope of the invention as it is set forth herein.

What is claimed is:

1. A process for treating a dinitroaniline which comprises contacting crude dinitroaniline one or more times with an effective amount of inorganic sulfite in aqueous solution at a pH of from 8 to 11, and at a temperature above the melting point of dinitroaniline and below the boiling point of water, the dinitroaniline being selected from the group consisting of trifluralin, benefin, ethalfluralin, isopropalin, butralin, pendimethalin, fluchloralin, profluralin, dintramine, chlornidine, oryzalin, nitralin, prosulfalin, and prodiamine.

2. A process according to claim 1 wherein the dinitroaniline treated is trifluralin, benefin, or ethalfluralin.

3. A process according to claim 1 wherein the sulfite is selected from the group consisting of sodium sulfite, potassium sulfite and ammonium sulfite.

4. A process according to claim 1 wherein the treatment is carried out at a temperature of from 60° C. to 90° C.

5. A process according to claim 1 where the treatment is applied more than once to the crude dinitroaniline.

* * * * *